United States Patent [19]

Molina

[11] 3,965,350
[45] June 22, 1976

[54] DYE PENETRANT METHOD FOR DETECTING FLOWS

[75] Inventor: Orlando G. Molina, Westminster, Calif.

[73] Assignee: Air Products and Chemicals, Inc., Allentown, Pa.

[22] Filed: June 17, 1974

[21] Appl. No.: 480,057

Related U.S. Application Data

[60] Division of Ser. No. 220,414, Jan. 24, 1972, which is a continuation-in-part of Ser. No. 68,475, Aug. 31, 1970, abandoned, which is a continuation of Ser. No. 655,752, July 25, 1967, abandoned.

[52] U.S. Cl. ............................ 250/302; 250/461 R; 252/301.19
[51] Int. Cl.² ........................................ G01N 21/38
[58] Field of Search .................. 250/302, 458, 461; 252/301.2 R, 301.2 P

[56] References Cited
UNITED STATES PATENTS

| | | | |
|---|---|---|---|
| 2,806,959 | 9/1957 | De Forest et al. | 250/302 |
| 3,311,479 | 3/1967 | Alburger | 252/301.2 P X |
| 3,386,920 | 6/1968 | Alburger | 252/301.2 P |
| 3,429,826 | 2/1969 | Alburger | 250/302 X |

*Primary Examiner*—Archie R. Borchelt
*Attorney, Agent, or Firm*—James C. Simmons; Barry Moyerman

[57] ABSTRACT

A dye penetrant composition adapted to enter minute surface defects when applied over a workpiece surface, which consists essentially of an organic dye, preferably a fluorescent dye, in a lactam solvent, particularly N-methyl-2-pyrrolidone, and providing improved clarity and definition when inspected under suitable, e.g. fluorescent, light.

8 Claims, No Drawings

DYE PENETRANT METHOD FOR DETECTING FLOWS

This application is a divisional of my copending application Ser. No. 220,414, filed Jan. 24, 1972, which is a continuation-in-part of my copending application Ser. No. 68,475, filed Aug. 31, 1970, now abandoned which in turn is a continuation of U.S. application Ser. No. 655,752, filed July 25, 1967, now abandoned.

This invention relates to an improved dye penetrant composition and method for non-destructively testing metal specimens to locate and identify surface voids or defects and more particularly to an improved liquid vehicle for such a dye penetrant.

Heretofore, it has been thought in the liquid dye penetrant inspection field that dye sensitivity was of dominant importance in achieving maximum clarity of a residual dye trace in revealing minute surface defects. The technical literature has noted the characteristic dimensional sensitivity of various dyes whereby, at a certain critical film thickness in an exuded film of residual dye, there exists a threshold of sensitivity below which the visibility of the trace substantially disappears. Elaborate methods for measuring dye sensitivity have been documented in the prior art, on the assumption that the best and clearest dye trace achievable in a given size of surface defect depended primarily upon the choice of dye used, and upon varying the thickness of the film identified with exuded dye to produce a visibile trace.

Moreover, dye penetrants known to the prior art are frequently applied by immersion of the workpiece in a dip tank filled with the dye penetrant, which involved tremendous cost in the case of large workpieces. Since the tank must be continually replenished due to evaporation of the penetrant, the cost of a large amount of penetrant required to fill the tank continually increases by such additions of penetrant.

The principal object of the present invention is to provide an improved penetrant composition and method for its use, particularly with regard to the vehicle thereof, capable of providing rapid inspection of workpieces with improved clarity, definition and versatility, and with low capital equipment costs.

In contrast with the foregoing prior art approach, the essential feature of the present invention is based on the principle that the clarity and definition of a dye trace, particularly a fluorescent dye trace, primarily depends, not on the type of dye used in a liquid dye penetrant, but upon the extent of dye concentration in the residual penetrant which remains within surface voids or defects whatever their dimensional size may be. In carrying out this principle and as the main concept of the present invention it has been found that by use of certain lactams, and more particularly certain N-lower alkyl 2-pyrrolidones, as vehicle for the penetrant dye, relatively high concentrations of dye, especially fluorescent dye, can be dissolved in such vehicle. The extremely low surface tension of such lactam or pyrrolidone vehicle and its high retentivity in minute flaws and microcracks, together with its high sensitivity and its ability to hold a high concentration of dye in solution, provide improved resolution and clarity of the dye trace and rapid efficient inspection of the workpiece.

According to the present invention, there is provided an improved homogeneous liquid dye penetrant composition which consists essentially of an N-lower alkyl-2-pyrrolidone vehicle as defined more fully below, and a dye, particularly a fluorescent dye, which is soluble in such pyrrolidone vehicle. The dye penetrant hereof can be used alone in a dye penetrant inspection method, or in conjunction with a developer coating, or an additive to enhance the effectiveness of penetrants known to the prior art. The dye which can be employed in conjunction with the pyrrolidone vehicle hereof can be any fluorescent or non-fluorescent dye which is soluble in such vehicle. Although the selection of any particular dye is not essential for use with the pyrrolidone vehicle, exemplary and preferred fluorescent and non-fluorescent dyes which are effective in the penetrant composition hereof are noted below.

The pyrrolidone vehicles useful according to the present invention are the substituted lactams in the form of the N-alkyl-2-pyrrolidones, the alkyl group being a short carbon chain of not more than 4 carbon atoms. These pyrrolidones accordingly have the general formula:

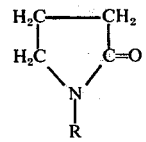

where R is a alkyl group containing from 1 to 4 carbon atoms. Examples of such groups are methyl, ethyl, propyl, isopropyl, butyl and isobutyl. Specific examples of these compounds are N-methyl-2-pyrrolidone, N-ethyl-2-pyrrolidone, N-propyl-2-pyrrolidone, N-isopropyl-2-pyrrolidone, N-butyl-2-pyrrolidone, and N-isobutyl-2-pyrrolidone.

A particularly stable N-alkyl substituted pyrrolidone having the foregoing general structure and which is especially preferred in practicing the invention is N-methyl-2-pyrrolidone. Such pyrrolidone solvent has a freezing point of about −24°C and a boiling point of 395°F, with a flash point of 204°F, and hence has low volatility and is ideally suited for use in the dye penetrant disclosed herein on a large industrial scale. Moreover, it has a low viscosity of 1.65 centipoise at 25°, which results in rapid and effective penetration of the penetrant in minute surface voids.

The immediately foregoing N-alkyl-2-pyrrolidones, and particularly N-methyl-2pyrrolidone, possess good spraying characteristics and require no soaking period to penetrate within minute surface voids.

The pyrrolidones hereof, particularly N-methyl-2-pyrrolidone, have the characteristic known as spontaneous mobility, which refers to the natural property in a liquid to creep over surfaces and into voids. Such property is demonstrated, for example, by the fact that a small quantity of the solvent having this property, placed in the bottom of a cup resting on a table top, will gradually creep up to the sides of the cup, over the edge and down the outer surfaces thereof, and will finally spread over the surface of the table top.

Of particular significance, the N-alkyl-2-pyrrolidones hereof, particularly N-methyl-2-pyrrolidone, have the ability to dissolve a large amount of dye per unit of volume while at the same time preventing or eliminating dye crystallization or precipitation in formulations of dye penetrant involving high concentrations of dye. This permits retention of the dye penetrant in the liquid state on the parts to be tested over any desired period of time without danger of precipitation or crystallization of the dye. In addition, these pyrrolidones, particularly N-methyl-2-pyrrolidone, are completely miscible in water, and hence this greatly facilitates water washability, as described in greater detail below. Also, the pyrrolidones hereof are entirely compatible with the dye component and all other optional components, including surfactants and other solvents, which can be added to the dye penetrant hereof, as described in detail hereinafter, preventing stratification of the dye penetrant due to long exposure to air, e.g. as in tanks. Moreover, the N-alkyl pyrrolidones hereof, particularly N-methyl-2-pyrrolidone, are essentially non-toxic, non-flammable and are relatively inexpensive.

As previously noted, various types of fluorescent and non-fluorescent dyes known to the prior art can be incorporated in the pyrrolidone vehicles hereof, and such dyes can be water-insoluble or water soluble.

Exemplary of fluorescent dyes which can be employed in the pyrrolidone-containing penetrant are the naphthalimide dyes having the formula:

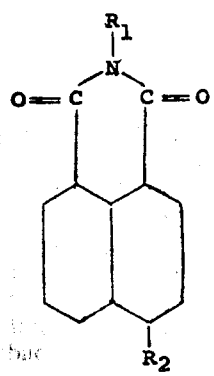

where $R_1$ is an alkyl chain such as methyl, ethyl, propyl, butyl, and the like, and $R_2$ is an amino group, which may be unsubstituted or substituted, e.g. by an alkyl chain such as methyl, ethyl, propyl, butyl, and the like. Specific dyes of this type are Calcofluor Yellow, Color Index—Fluorescent brightening agent No. 4: Fluorol 7 GA, Color Index—Fluorescent brightening agent 75; and Azosol Brilliant Yellow 6 GF, Color Index—Solvent yellow 44. These dyes are similar in structure except for the $R_1$ and $R_2$ substituents in the structural formula above.

Other dyes which may be employed in the penetrant composition include, for example, fluorescent xanthene dyes such as the rhodamines e.g. Rhodamine B, Color Index 45170, and Rhodamine 6 GDN, Color Index 45160. Also Auramine, Color Index 41,000, and Eosine G, Color Index 45380, can be employed. These dyes fluoresce in a color range from greenish yellow to red.

Other fluorescent dyes which I have found suitable are the coumarin derivatives, as exemplified by the dyes having the following formula:

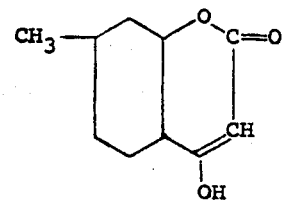

Exemplary coumarin derivatives which can be employed are Calcofluor White RW, Color Index—Fluorescent brightening agent 68, and Blancophor White AW, Color Index—Fluorescent brightening agent 68.

Additional useful dyes include Brilliant Sulfo Flavine FFA, the condensation product of 4-amino-3-sulfonaphthalic anhydride and p-toluidine, Color Index 56205, and Blancophor FFG fluorescent dye, Color Index—Fluorescent brightening agent 61.

A particularly effective fluorescent dye for the present purpose is the above-noted Fluorol 7 GA.

The fluorescent dyes provide the advantage of often not requiring application of a developer, although an activating agent may be used where the brilliance of residual fluorescent dye is improved thereby.

Although fluorescent brightening agents are generally not necessary for addition to the penetrant hereof, e.g. a dye penetrant composed of N-methyl-2-pyrrolidone combined with Fluorol 7 GA dye, since the pyrrolidone hereof has a strong activating effect on the fluorescent dye without requiring any other aids in this respect, where inspection test conditions involving fluorescent dye are hampered by excessive daylight or poorly concentrated ultraviolet light, increased brilliance of residual dye may be obtained by minor additions of a suitable brightening agent such as known to the prior art as taught in U.S. Pat. No. 2,920,203, issued Jan. 5, 1960, and also exemplified by the above coumarin derivatives such as Calcofluor White RW. Alternatively, increased brilliance of a dye trace may be obtained by adding a powdered or other developer adapted to activate the dye more highly, although some of the dye penetrants disclosed herein need no developers, as discussed below.

There can also be employed non-fluorescent or daylight type dyes such as azo type dyes, e.g. xyleneazo-beta-naphthol, Mefford No. 322 dye, believed to be o-tolueneazoxyleneazo-beta-naphthol, and the azo dyes marketed as Oil Red "O" and Sudan Red. These dyes can be employed where daylight or white light is only available and the size of the cracks and flaws in the surface of the object to be tested is relatively large. However, for small cracks or microcracks, and which are extremely narrow, as produced for example, by stress corrosion or fatigue cracking, it is preferred to employ fluorescent dyes having greater sensitivity or detectability as result of the high contrast obtained by the fluorescent indications.

The absence of sulfur or chlorine atoms in the essential components of the dye penetrant composition makes it useful for inspecting nickel alloy and titanium workpieces. Thus, the present invention provides a dye penetrant composition having improved compatibility with titanium, nickel and other materials which are adversely affected by chlorine or sulphur atoms commonly found in prior art penetrants. In addition, the invention provides a dye penetrant which under ordinary environmental conditions is substantially non-flammable, slow evaporating, and the consistency of which may be increased without a significant loss in its penetrating effectiveness, so that vertical and overhead surfaces can be inspected by application of the penetrant without runoff or the like.

It is a particularly significant feature of the concept disclosed herein that the pyrrolidone vehicle used in combination with the foregoing dyes is capable of dissolving an extremely large amount of dye per unit of vehicle volume. For example, a ratio of up to two parts of dye to one part of pyrrolidone vehicle by volume can be employed, about one-half part dye to one part vehicle being satisfactory, while a ratio of about one to one by volume in some instances is preferred. The ratio of dye to solvent can range, for example, from about one part of dye to about 25 parts of pyrrolidone, to about two parts of dye to about one part of pyrrolidone, by volume.

The amount of residual dye remaining in minute surface cracks or defects, especially of microscopic size, is necessarily extremely minute. Since the dye constituent of the penetrant is solely responsible for the coloration or fluorescing effect required to produce a visible indication of the defect, it follows that a low concentration of dye in the minute quantity of residual penetrant within a defect will inhibit or prevent any visible indication. Accordingly, the present pyrrolidone dye penetrant vehicle, which is capable of dissolving and maintaining a very high concentration of dye, will have correspondingly greater effectiveness in producing the necessary trace for inspection purposes.

As a further significant feature of the present invention, it has been found that the use of the pyrrolidone hereof, e.g. N-methyl-2-pyrrolidone, as a vehicle in dye penetrants affords the very significant advantage of often rendering unnecessary a developing step. Thus, the spontaneous creeping characteristics of the vehicle assures its entry into extremely minute microscopic surface defects such as 10/15 millionths of an inch in width and further assures exudation of residual dye from such defects, while the high dissolving power of the pyrrolidones hereof results in a great concentration of residual dye in the defects.

The high miscibility of the pyrrolidone vehicle hereof, e.g. N-methyl-2-pyrrolidone, with water affords the very useful advantage of permitting rapid cleaning of dye penetrant from the specimen surface by the application of water thereto without the intermediate use of emulsifiers or the like. In contrast to the above, most water washable dye penetrants in commercial use and known to the prior art have a glycol base or are oil based and include strong emulsifiers in the penetrant composition to facilitate cleaning thereof, but which results in excessive removal of residual dye from surface defects during the cleaning step, whereby the amount of dye remaining in microscopic defects is insufficient to produce a visible dye trace for inspection purposes. The foregoing characteristic of glycol and oil type penetrants severely limits their sensitivity and hence their usefulness. In the present case, in order to aid in rendering the dye penetrant, e.g. as described in Examples II and III below, water washable, the addition of a surfactant has been found generally preferable. The pyrrolidone, e.g. N-methyl-2-pyrrolidone, is water miscible and leaves the specimen surface immediately when water is applied thereto, whereas the dye constituent is not water miscible, and hence tends to coat the entire specimen surface. The surfactant functions to suppress the rate of miscibility of such pyrrolidone vehicle in water, thus allowing the excess dye to be carried off in the vehicle upon application of water, but leaving the remainder of the penetrant solution in the cracks and flaws.

The choice of surfactants may vary widely among commercially available surfactants, but in any case should be compatible with the dye used in the penetrant. Thus, a water soluble nonionic detergent such as Tergitol nonionic NPX, a hydrophilic nonionic detergent containing etheroxygen groups, is preferred in combination with the pyrrolidone, e.g. N-methyl-2-pyrrolidone, to render the dye penetrant completely water washable, although Tergitol nonionic TMN and Aerosol OT 75% also can be employed. An increase of viscosity in the penetrant may result from the addition of the detergent or surfactant, but the spontaneous mobility or creeping characteristic of the vehicle combined with high concentration of dye therein results in rapid and complete entry of the penetrant with a substantial quantity of dye into microscopic defects notwithstanding the above-mentioned increase of viscosity. Tergitol nonionic NPX is a nonyl phenyl ether of polyethylene glycol containing 10.5 mols of ethylene oxide and having the general formula $C_9H_{19}C_6H_4O(CH_2CH_2O)_{10.5}H$. Tergitol TMN is trimethyl nonyl ether of polyethylene glycol containing six mols of ethylene oxide and has the formula $(CH_3)_3C_9H_{16}O(CH_2CH_2O)_6H$. Aerosol OT 75% is a 75 wt % solution in water of dioctyl sodium sulfo-succinate. Other nonionic surfactants are also usable in the water washable penetrant disclosed herein to produce essentially the same results, provided that such surfactants are sufficiently hydrophilic in nature.

Thickening agents can also be incorporated into the dye penetrant composition of the invention, to permit the dye penetrant to be applied on vertical or overhead surfaces. Such agents can include, for example, fumed silica, fine particle alumina and gums which are compatible with the other components of the dye penetrant composition.

As a further significant feature of the invention, it has been found that any dye penetrant containing the pyrrolidone vehicle hereof, e.g. N-methyl-2-pyrrolidone, and a water-soluble surfactant such as those mentioned above, can be beneficially augmented in effectiveness by the addition of water-insoluble solvents or surfactants, an example being a ketone such as isobutyl heptyl ketone, methyl ethyl ketone, and the like, or surfactants which are similarly water insoluble. The combination of water-soluble and water insoluble components is usable in water-washable liquid dye penetrants of the invention wherein the composition may vary over an extremely wide range depending upon the type and nature of the workpiece material and the size or type of defect which is sought to be disclosed.

Water insoluble surfactants such as Tergitol nonionic NP-14, which is nonyl phenyl polyethylene glycol ether having the formula $C_9H_{19}C_6H_4O(CH_2CH_2O)_4H$, tend to retard water washability of the penetrant whereby greater water contact is required to clean the dye penetrant from the specimen surface than would result for the same penetrant without Tergitol nonionic NP-14, and such detergent can, for example, be employed in combination with Tergitol nonionic NPX. Since residual dye penetrant within minute surface cracks and defects is not exposed to as much water force or amount of water as the excess dye penetrant on the specimen surface, the stated retarding effect of Tergitol nonionic NP-14 resists the removal of such residual dye penetrant, and the defects retain more penetrant following the water-washing step than they otherwise would. The foregoing characteristic results in a particular adaptability of such dye penetrant for use with defects of microscopic size requiring powerful magnification in order to be seen. The use of a combination of Tergitol nonionic NPX and Tergitol nonionic NP-14 for this purpose is described in Example XI below. Other water-insoluble surfactants such as Triton X-15 and Triton X-35 are equivalent to Tergitol nonionic NP-14 and may be substituted in place thereof. The Triton nonionic surfactants are commonly described as alkyl aryl polyether alcohols.

It has been found that wide variation in the proportional content of the respective components of the dye penetrant of the invention can be tolerated, as illustrated by the examples below. Thus, the compositions of Examples XII and XIII below, for example, are useful in varying degrees of sensitivity over the volumetric range of from about 1/2 to about 6 parts of dye, from about 1 to about 12 parts of the pyrrolidone, from about 5 to about 45 parts of ketone solvent, and from about 1 to about 30 parts of surface active agent, e.g. water soluble surface active agent. Generally, each incremental increase of surfactant in the foregoing range of variation is accompanied by a slight but perceptible incremental decrease in sensitivity, but the penetrant which results even from the highest proportion of surfactant possesses greater effectiveness in disclosing defects of relatively large size or in rough surfaces such as castings and the like, than penetrants known to the prior art. Also, the larger proportion of pyrrolidone is accompanied by a greater dye concentration in the resulting penetrant, although the amount of dye, or combination of dye and brightening agent therefor in the case of fluorescent dyes, may optimally correspond approximately with the amount of pyrrolidone in many cases.

In employing my novel dye penetrant composition of the invention, in a dye penetrant inspection method for detecting cracks and flaws on the surface of a body, e.g. a metal surface, the process comprises applying to such surface a homogeneous liquid dye penetrant consisting essentially of the N-substituted-2-pyrrolidone solvent and dye, e.g. fluorescent dye component, removing excess liquid penetrant from said surface, a portion of such dye penetrant remaining in the cracks and defects, and viewing the surface of the body under suitable light conditions, e.g. ultraviolet or black light when the dye in the dye penetrant is a fluorescent dye, to locate any cracks or defects on the surface of the body, as indicated by colored traces, for example, by fluorescent emissions, from the dye therein.

When the liquid dye penetrant is employed in conjunction with a developer, either in liquid or solid form, following application of the dye penetrant and removal of excess penetrant, the developer composition is applied to the part surface and excess developer composition is removed from the surface, as by means of a gentle air blast when employing a solid powder developer composition.

More particularly, in carrying out such method, if necessary, the part or surface to be inspected first can be suitably prepared as for example by suitably cleaning and drying the specimen.

The liquid dye penetrant is then applied to the test specimen, e.g. by dipping same into a bath of the penetrant, or the penetrant can be poured or sprayed onto the surface of the test specimen. The dye penetrant composition is maintained on the surface of the test body or specimen for a period sufficient to permit the composition to penetrate the cracks and imperfections in the part surface, e.g. for about 1 to about 5 minutes.

The fluorescent penetrant composition is then removed or washed off the surface of the part being tested, without being removed from the openings of the surface cracks or flaws. This can be accomplished by any suitable means such as by wiping with a cloth, or a solvent impregnated cloth, or with water. Where the penetrant composition is not water washable, it can be removed by addition thereto of a suitable emulsifying agent. Thus for example excess penetrant hereof can be removed from the test specimen by application of a sprayed mixture of air and water.

The following examples serve to illustrate but are not limitative of, the benefits and advantages obtained by practice of the present invention. The statement of results in each case relates to the sensitivity or ability of the penetrant tested in detecting microcracks approximately one/nineteen millionth of an inch in width on the surface of chrome plated steel and chrome plated copper specimens, and all specific concentrations are given with respect to volume.

EXAMPLE I

A homogeneous liquid dye penetrant comprising one part of N-methyl-2-pyrrolidone, one part of isobutyl heptyl ketone and two parts of Fluorol 7 GA dye was applied by moistening an absorbent material with the liquid penetrant and wiping the same across the specimen surface. Thereafter, the specimen surface was superficially cleaned by lightly rubbing with a cleaning agent comprising a mixture of one part pine oil, one part nonionic detergent and five parts of distilled water. Following the cleaning step, the specimen surface was spray coated with a developer comprising about 19% vinyl chloride-vinyl acetate copolymer resin, 1% white mineral oil, about 61% toluene, about 14% methyl ethyl ketone, 6% diisoctyl phthalate, and a nominal amount of non-chalking titanium dioxide. The sprayed coating immediately revealed dye traces of such close proximity as to be barely distinguishable without microscopic aid but which was found to delineate a very complex pattern of herringbone and web cracks when viewed under a microscope.

EXAMPLE II

A homogeneous liquid penetrant comprising two parts of N-methyl-2-pyrrolidone and one part of Fluorol 7 GA dye was applied to a specimen surface by brushing, after which cleaning was accomplished as in Example I above, and the surface was coated with a developer conforming with that used in Example I above. The sensitivity and penetrability of this mixture were found to produce excellent clarity and delineation of microcracks in the tested surface.

EXAMPLE III

The liquid dye penetrant corresponding with that described in Example II above but comprising five parts of N-methyl-2-pyrrolidone and one part of Fluorol 7 GA dye was tested using the same procedure as described for the liquid dye penetrant of Example I above. The dye trace obtained upon application of the developer coating revealed excellent clarity and definition but slightly less in brilliance compared with the liquid penetrant described in Example II. Thereafter, a dye penetrant in liquid form comprising ten parts of N-methyl-2-pyrrolidone and one part of Fluorol 7 GA dye was tested in the same manner as the five to one dye penetrant mixture, and was found to produce acceptable visibility and definition but significantly less brilliance and clarity than the dye penetrant discussed in Example II above.

EXAMPLE IV

A liquid dye penetrant comprising one part of N-methyl-2-pyrrolidone, nine parts of isobutyl heptyl ketone, and one part of Fluorol 7 GA fluorescent dye was tested using the procedures described for the liquid dye penetrant set forth in Example I above. Although good sensitivity and penetrability of the penetrant mixture were evidenced by the delineation of microcracks in the resulting dye pattern, the brilliance and overall sensitivity of the penetrant were less than that obtained from the dye penetrants described in Examples I and II.

EXAMPLE V

A penetrant comprising ten parts of N-methyl-2-pyrrolidone and one part of daylight visible Oil Red "O" dye was tested on a specimen surface as in Example I above. Good clarity and definition of the dye trace pattern were obtained following application of the developer, but the daylight visible dye trace was less perceptible than the brilliance of the fluorescent dye trace obtained from the ten to one ratio test in Example III above.

EXAMPLE VI

A penetrant comprising two parts of N-methyl-2-pyrrolidone and one part of daylight visible Oil Red "O" dye was tested on a specimen surface as in Example I above. The clarity and definition of the dye trace pattern obtained following application of a developer coating were good. However, it was noted that a smaller amount of the daylight visible dye could be dissolved in a given quantity of the vehicle than the Fluorol 7 GA dye used in Examples I and II above.

The following examples illustrate the novel inspection material and process applicable thereto in a completely water washable penetrant system requiring no developer. The final dye trace may sometimes be enhanced in brilliance by use of a developer, but the penetrants disclosed in these examples have been found entirely satisfactory without developers, and hence use of the latter in these examples may be termed optional.

EXAMPLE VII

The following homogeneous liquid dye penetrant composition was prepared:

|  | Parts by Volume |
| --- | --- |
| N-methyl-2-pyrrolidone | 25 |
| Tergitol nonionic NPX | 3 |
| Fluorol 7 GA dye | 1 |
| Calcofluor White RW | 1 |

The penetrant was applied by brushing on the surface of aluminum test blocks which had been cracked by heating to an elevated temperature and then plunged into water. The penetrant was allowed to dwell for 20 seconds, then the specimen was washed by a sprayed mixture of air and water to remove excess penetrant. This was followed by a blast of air to accelerate the drying of residual water on the specimen surface. The specimen was viewed under ultraviolet light with the aid of a microscope. Residual dye traces of excellent definition and brilliance were observed, with relatively little background fluorescing.

Following the above, a coating of developer corresponding to that used in Example I above was lightly sprayed on the specimen surface to determine if the brilliance or clarity of the dye trace would be improved by action of the developer. No perceptible change in the dye trace was observed to result from such developer.

The same formulation of penetrant in the example was tried with Tergitol nonionic TMN substituted in place of Tergitol nonionic NPX and in the same proportion. Good water washability of the dye penetrant resulted, and the same high quality and definition of dye trace.

Thereafter, the penetrant in this example was prepared with Aerosol OT 75% substituted in place of Tergitol nonionic NPX and in the same proportion. Again, good water washability and excellent clarity in the dye trace resulted.

EXAMPLE VIII

The following homogeneous liquid dye penetrant composition was prepared:

|  | Parts by Volume |
| --- | --- |
| N-methyl-2-pyrrolidone | 15 |
| Tergitol nonionic NPX | 10 |
| Fluorol 7 GA | 1 |
| Calcofluor White RW | 1 |

The penetrant application to the specimen surface and subsequent cleaning steps were both as set forth in Example VII above. Excellent dye trace results were obtained, revealing very small quench cracks.

The above composition of this example was varied in regard to proportions of the Fluorol 7 GA dye and the Calcofluor White RW brightener from one part of each to one-fourth part each, by volume, the other constituents and proportions remaining unchanged. Excellent dye trace patterns were obtained uniformly throughout the stated range of variation, although a slightly lesser sensitivity of the dye penetrant was observed in the lowest range of dye content compared with the highest. Also, it was found that the brilliance and sensitivity of the mixture were unchanged by omission of the Calcofluor White RW constituent provided that the amount of Fluorol 7 GA dye is doubled. Thus, in the formulation set forth above in this example, essentially the same result is obtained if two parts of Fluorol 7 GA dye are used and the one part of Calcofluor White RW is omitted.

EXAMPLE IX

The formulation of Example VIII above was used for inspection of porous workpiece materials, notably iron castings, and found to provide excellent results provided that an emulsifier is used to remove most of the excess dye just prior to washing by water spray. Suitable emulsifiers were found to include many commerical products known to the prior art. Also, acetone, ketones such as methyl ethyl ketone, and trichlorethylene, when followed immediately by water spraying, are useful in removing excess penetrant in the process according to this example.

EXAMPLE X

The formulation of Example VIII above was used with water-soluble dyes substituted in place of Fluorol 7 GA dye and the omission of Tergitol nonionic NPX detergent. The water-soluble dyes in modern commercial use for liquid dye penetrants consist of the same dyes used for water-insoluble penetrants with the exception that the dyes are treated with so-called cutters to make the dyes water soluble. These cutters are acids, as a result of which the dye penetrants using water-soluble dyes are acidic and therefore detrimental to many workpiece materials such as titanium. Two of the water-soluble dyes substituted in place of Fluorol 7 GA dye from Example VIII above were Brilliant Sulpho Flavine FFA, the condensation product of 4-amino-3-sulfo naphthalic anhydride and p-toluidine, Color Index 56205, and Blancophor FFG fluorescent dye. Use of water-soluble dyes in place of Fluorol 7 GA dye in the penetrant formulation of Example VIII above was found to render unnecessary the surfactant, whereby the Tergitol nonionic NPX was omitted.

Use of the foregoing modified water-soluble dye penetrants was found to produce good sensitivity and strong dye traces in gross defects and relatively larger cracks than quenching cracks. However, water-soluble dyes were found to produce less brilliant dye traces than water-insoluble dyes and were less stable for minute crack detection. Also, water-soluble dyes resulted in a noticeable lack of background effects which refers to contamination of the total workpiece surface even with careful cleaning thereof and which tends to interfere with clarity of the dye trace produced by surface defects.

The following examples serve to illustrate the use of water-soluble and water-insoluble surfactants in the liquid dye penetrant of the invention.

EXAMPLE XI

The following homogeneous liquid dye penetrant was prepared:

|  | Parts by Volume |
|---|---|
| N-methyl-2-pyrrolidone | 2½ |
| Isobutyl heptyl ketone | 7½ |
| Tergitol nonionic NPX | 5 |
| Tergitol nonionic NP-14 | 7½ |
| Calcofluor White RW | 2 |
| Fluorol 7 GA | .66 |

The foregoing dye penetrant was applied by brushing on specimens corresponding to those described for Example VII above and cleaned by a sprayed mixture of air and water. When viewed under ultraviolet light with the aid of a microscope, residual dye traces of extreme brilliance and excellent definition were observed to reveal an intricate pattern of microscopic quenching cracks. No developing agents were necessary to activate the fluorescent dye or to raise the dye pattern above the threshold of visibility. However, in certain instances, such as surface type cracks such as stress corrosion cracking, a developing agent is desirable to enhance the brilliance of the dye indication.

In the dye penetrant of this example, N-methyl-2-pyrrolidone may be appropriately termed the primary solvent for the dye and results in a much higher dye concentration than could otherwise be achieved in the final dye penetrant.

Isobutyl heptyl ketone as used in the penetrant composition of this example augments the spontaneous exudation, creeping and wetting properties of the N-methyl-2-pyrrolidone, as described above, and for convenience is termed a secondary solvent for the dyes.

Tergitol nonionic NPX in the formulation of this example functions mainly to permit water washability of the dye, but also augments the wetability of the penetrant solution and improves the brilliance of the final dye pattern. Aerosol wetting agents such as Aerosol OT 75% noted above can also be employed, e.g. substituted for Tergitol nonionic NPX.

Excellent results can be achieved with the same dye penetrant disclosed in this example even when Tergitol nonionic NP-14 is omitted therefrom, but with a lesser sensitivity or ability of the final dye trace to delineate defects of microscopic size as small as those detectable with the formulation set forth initially in this example.

EXAMPLE XII

The following homogeneous liquid dye penetrant was prepared:

|  | Parts by Volume |
|---|---|
| N-methyl-2-pyrrolidone | 2½ |
| Isobutyl heptyl ketone | 20 |
| Tergitol nonionic NPX | 15 |
| Calcolfluor White RW | 2 |
| Fluorol 7 GA | .66 |

The penetrant having this composition provides excellent sensitivity although slightly less than that set forth in Example XI above. The main advantage of the penetrant in this example in comparison with that of Example XI is its significantly lower viscosity whereby the penetrant in this example can be sprayed onto the specimen surface rather than by brushing or by immersing the specimen therein. The penetrant in this example, as in all of the penetrants disclosed herein, was found to be completely compatible with all developing agents known to the prior art and commercially available. Unlike some of the other penetrants disclosed herein, the penetrant in this example produced a dye trace which responded to developers, especially dry powder type developers by an increase of fluorescent brilliance.

Of the various dye penetrants disclosed herein, those which include Tergitol nonionic NPX were tested with certain other water-soluble surfactants substituted in place of Tergitol nonionic NPX and substantially the same results as discussed above were obtained with each of the substituted materials in the various dye penetrants. The substituted materials which were separately tried in each case were Triton X-100, Triton X-102, Triton X-114, Triton X-155 and Triton X-305 as well as Aerosol OT 75%. Triton X-100, X-102, X-114 and X-305 are similar chemically to X-15 and X-35, having 9-10; 12-13; 7-8; and 35 condensed glycol groups, respectively. Triton X-155 is an alkylaryl polyether alcohol.

It was further discovered that the complete omission of a water-soluble surfactant such as Tergitol nonionic NPX, from the penetrant compositions disclosed herein which include the same, resulted in little or no compromise in the sensitivity or effectiveness of the dye penetrant with respect to the final dye trace. The principal difference associated with omission of the water-soluble surfactant is that the resulting penetrant solution is not water soluble but is easily removable during the cleaning step by use of standard commercially available emulsifiers or gels and does not require the use of oils.

EXAMPLE XIII

The following liquid dye penetrant was prepared:

|  | Parts by Volume |
| --- | --- |
| N-methyl-2-pyrrolidone | 7 |
| Isobutyl heptyl ketone | 45 |
| Tergitol nonionic NP-14 | 30 |
| Calcofluor White RW | 6 |
| Fluorol 7 GA | 3 |

The foregoing penetrant composition was applied by brushing on aluminum test blocks containing quenching cracks of microscopic size. Excess penetrant was thereafter cleaned from the specimen surface using a combination spray of water and air. It was found that standard commercial emulsifiers and gels could alternatively be used in the cleaning step in place of a water-air spray, although the latter method results in maximum sensitivity of penetrant performance as may be desired in special cases. Although Tergitol nonionic NP-14 resists removal of the penetrant by water, the dye appears to have sufficient solubility in isobutyl heptyl ketone whereby removal of the latter by water contact simultaneously removes the excess dye contained within the isobutyl heptyl ketone. When N-methyl-2-pyrrolidone is used with the same dye without the presence of a secondary solvent for the dye, water contact results in immediate removal of the N-methyl-2-pyrrolidone and leaves the dye coated continuously over the specimen surface in a manner which prevents useful inspection results, as mentioned hereinabove.

EXAMPLE XIV

The dye penetrant composition and procedure of Example I are followed employing in place of the pyrrolidone thereof, the same amount of N-ethyl-2-pyrrolidone.

Results similar to Example I are obtained.

EXAMPLE XV

The dye penetrant composition and procedure of Example II are followed employing in place of the pyrrolidone thereof, the same amount of N-ethyl-2-pyrrolidone.

Results similar to Example II are obtained.

EXAMPLE XVI

The dye penetrant composition and procedure of Example XI are followed employing in place of the pyrrolidone thereof, the same amount of N-propyl-2-pyrrolidone.

Results similar to Example XI are obtained.

EXAMPLE XVII

The dye penetrant composition and procedure of Example I are followed except employing in place of Fluorol 7 GA, the same amount of the fluorescent dye Rhodamine B.

Bright fluorescent dye traces comparable to the results in Example I are obtained.

EXAMPLE XVIII

The dye penetrant composition and procedure of Example VII are followed, employing in place of Fluorol 7 GA and Calcofluor White RW, 2 parts by volume of Auramine.

Brilliant residual dye traces similar to the results in Example VII are obtained.

EXAMPLE XIX

The dye penetrant composition and procedure of Example XI are followed, except employing in place of the Calcofluor White RW and Fluorol 7 GA, 2 parts by volume of Calcofluor Yellow and 0.66 part by volume of Blancophor White AW.

Residual dye traces of high brilliance and definition are obtained when this specimen is viewed under ultraviolet light.

In addition to the specific results and advantages disclosed for the dye penetrants disclosed hereinabove, it is a particular advantage that such penetrants are characterized by extreme stability and low evaporation rate. Thus, for example, over a period of 30 days, a measured quantity of the liquid dye penetrant corresponding with that disclosed in Example VII above was allowed to remain in a stationary container together with a corresponding quantity of ten other liquid dye penetrants sold commercially and widely used in industry. Several of the commercially known dye penetrants were noticeably unstable in that they precipitated out of solution, but absolutely no trace of instability was found during the test period for the mentioned dye penetrant of Example VII herein, and the liquid dye penetrant thereof remained homogeneous and with no signs of precipitation or crystallization throughout this entire period. Moreover, the proportion of volume lost through evaporation from the measured quantity of material remaining compared with that initially contained at the start of the test was found to be substantially less for the dye penetrant of Example VII in this case than for any of the other dye penetrants tested. The significance of this advantage is best appreciated in the case of large open tank installations for liquid dye penetrant testing of large workpieces by immersion, wherein the cost of filling such tanks is very expensive. With further regard to the advantages of the liquid dye penetrant compositions disclosed herein, it has been found that the operating range of temperatures with respect thereto varies from a low of approximately 40°F to a high of about 200°F.

It has also been found that the various advantages described above and obtained by use of the dye penetrant hereof can also be achieved when such penetrants are combined with prior art penetrants.

The dye penetrant composition of the invention can be employed for penetrant inspection of cracks and microcracks in the surface of bodies of various materials, including, in addition to metals and allows thereof, such as titanium, nickel, steel, copper and aluminum, other materials such as ceramics, glass, plastics and rubber.

It is known in the prior art as disclosed in U.S. Pat. No. 3,386,920, to employ N-vinyl-2-pyrrolidone as solvent in a dye penetrant composition. However, the latter pyrrolidone does not possess the superior dissolving characteristics of the N-lower alkyl-2-pyrrolidones hereof, particularly N-methyl-2-pyrrolidone. In addition the N-vinyl-2-pyrrolidone has substantially less miscibility in water as compared to the N-lower alkyl-2-pyrrolidones, e.g. the N-methyl derivative hereof, and hence the use of such N-vinyl-2-pyrrolidone in dye penetrants presents problems of water washability. In addition the N-vinyl-2-pyrrolidone, particularly upon contact with or addition of water, emits a highly obnoxious odor, rendering it highly unsuitable for handling by operating personnel.

Since various changes and modifications of the invention will occur to and can be made readily by those skilled in the art without departing from the inventive concept, the invention is not to be taken as limited except by the scope of the appended claims.

I claim:

1. A method for detecting cracks and flaws in the surface of an object which comprises applying to said surface a homogeneous liquid penetrant composition which consists essentially of an N-alkyl-2-pyrrolidone, as vehicle, and a fluorescent dye which is soluble in said pyrrolidone, said pyrrolidone having the general formula

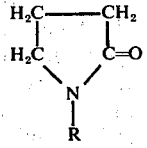

where R is an alkyl group containing from 1 to 4 carbon atoms; removing excess liquid penetrant composition from said surface, a portion of said liquid penetrant remaining in said cracks and flaws therein; and viewing the surface of said body under fluorescigenous light to obtain colored traces from the dye in said cracks and flaws.

2. The method as defined in claim 1, said pyrrolidone being N-methyl-2-pyrrolidone.

3. The method as defined in claim 1, said pyrrolidone being N-methyl-2-pyrrolidone, said fluorescent dye being selected from the group consisting of fluorscent naphthalimide, xanthene and coumarin dyes, the ratio of said dye to said pyrrolidone ranging from about one part of dye to about 25 parts of pyrrolidone, to about 2 parts of said dye to about 1 part of pyrrolidone, by volume.

4. The method as defined in claim 1, wherein said liquid penetrant composition includes hydrophilic nonionic detergent containing ether-oxygen groups as a surfactant.

5. The method as defined in claim 1, said liquid penetrant composition including isobutyl heptyl ketone.

6. The method as defined in claim 4, said surfactant being selected from the group consisting of a nonyl phenyl polyethylene glycol ether, a trimethyl nonyl ether of polyehtylene gly glycol and an alkyl aryl polyether alcohol.

7. The method as defined in claim 3, wherein said liquid penetrant composition includes hydrophilic nonionic detergent containing ether-oxygen groups as a surfactant and isobutyl heptyl ketone.

8. The method as defined in claim 3, said liquid penetrant composition containing a nonyl phenyl polyethylene glycol ether surfactant and isobutyl heptyl ketone.

* * * * *

UNITED STATES PATENT AND TRADEMARK OFFICE
CERTIFICATE OF CORRECTION

PATENT NO. : 3,965,350
DATED : June 22, 1976
INVENTOR(S) : Orlando G. Molina

It is certified that error appears in the above-identified patent and that said Letters Patent are hereby corrected as shown below:

In the title, change "FLOWS" to -- FLAWS --

Column 1, Line 5, after "1972" and before "which", insert
-- now U.S. Patent 3,838,160 --

Column 2, Line 48, "25°" should be -- 25°C --

Column 14, Line 68, "allows" should be -- alloys --

Signed and Sealed this

Fourteenth Day of June 1977

[SEAL]

Attest:

RUTH C. MASON
*Attesting Officer*

C. MARSHALL DANN
*Commissioner of Patents and Trademarks*